United States Patent [19]

Kawabata et al.

[11] 4,233,461
[45] Nov. 11, 1980

[54] PROCESS FOR PREPARING COLORLESS METHIONINE

[75] Inventors: Toshio Kawabata; Toshio Ishiyama, both of Niihama, Japan

[73] Assignee: Sumitomo Chemical Company, Limited, Osaka, Japan

[21] Appl. No.: 24,462

[22] Filed: Mar. 27, 1979

[30] Foreign Application Priority Data

Apr. 3, 1978 [JP] Japan .................................. 53/39598

[51] Int. Cl.$^3$ ........................................ C07C 149/247
[52] U.S. Cl. .................................................. 562/554
[58] Field of Search ............................... 562/559, 554

[56] References Cited

U.S. PATENT DOCUMENTS

| | | | |
|---|---|---|---|
| 2,557,913 | 6/1951 | Livak | 562/559 |
| 2,557,920 | 6/1951 | White | 562/559 |
| 3,917,683 | 11/1975 | Ouchi | 562/559 |
| 3,931,307 | 1/1976 | Eikelmann | 562/559 |

OTHER PUBLICATIONS

Kirk–Othmer, "Encyclopedia of Chemical Technology," 2nd Ed., vol. 3, pp. 550–567 (1964).

*Primary Examiner*—Natalie Trousof
*Assistant Examiner*—Michael Shippen
*Attorney, Agent, or Firm*—Stevens, Davis, Miller & Mosher

[57] ABSTRACT

Methionine devoid of a coloring matter can be obtained from the aqueous solution of alkali salts of methionine prepared by hydrolysis of 5-($\beta$-methylmercaptoethyl)-hydantoin with an alkali by decolorizing the said solution with reducing sulfur compound and thereafter collecting methionine as colorless crystals.

10 Claims, No Drawings

PROCESS FOR PREPARING COLORLESS METHIONINE

The present invention relates to a process for producing methionine. More particularly, the invention pertains to an improved method for preparing methionine devoid of a coloring matter from crude aqueous solution of alkali salts of methionine obtained by hydrolysis of 5-(βmethylmercaptoethyl)-hydantoin (hereinafter referred to as MMH) with an alkali.

It is known that methionine can be prepared by hydrolyzing MMH with an alkali such as sodium hydroxide, neutralizing the resulting alkali salts of methionine with an acid in aqueous medium, and thereafter crystallizing and collecting methionine therefrom. For this purpose, MMH is prepared, in general, by reacting acrolein with methyl mercaptan, and reacting the resulting β-methylmercaptopropionaldehyde with hydrogen cyanide and ammonium bicarbonate (Carbon dioxide and ammonia may be used in place of ammonium bicarbonate.), or reacting acrolein, methyl mercaptan, hydrogen cyanide, and ammonium bicarbonate (or carbon dioxide and ammonia) in the presence of a suitable catalyst (e.g., acetic acid). However, the aqueous solution of alkali salts of methionine prepared by such methods usually contains a certain coloring matter. Accordingly, in hitherto known processes, for example, the crude aqueous solution of methionine is treated with activated carbons or some other adsorbents, thereby adsorbing the coloring matters (Japanese Patent Publication No. 818/74), or a suitable orgaic solvent such as acetone is added thereto to precipitate methionine as colorless crystals (Japanese Patent (unexamined) Publication No. 86819/73). But, these methods have certain disadvantages. For instance, some extra work or arrangements for removal and reactivation or disposal of a large amount of the adsorbents used in the former method, and for recovery of the solvents used in the latter method are required.

In order to provide a more convenient and economical method for preparing methionine devoid of a coloring matter, an extensive study has been made, and, as the result, it has been found that the crude aqueous solution of alkali salts of methionine prepared by hydrolysis of MMH with an alkali, which is usually pale yellowish or yellowish brown and contains, in general, 2 to 20% by weight of alkali salts of methionine, can conveniently and economically be decolorized by adding a small amount of a reducing sulfur compound thereto, and colorless methionine can easily be obtained therefrom.

Thus, the present invention provides a process for preparing methionine devoid of a coloring matter from the aqueous solution of alkali salts of methionine prepared by hydrolysis of MMH with an alkali, which comprises treating the aqueous solution of alkali salts of methionine and/or the aqueous solution of methionine, which is obtained by neutralizing the said aqueous solution of alkali salts of methionine with an acid, with a reducing sulfur compound, and thereafter collecting methionine devoid of a coloring matter from the decolorized solution of methionine.

According to the present invention, methionine devoid of a coloring matter can be obtained by decolorizing the aqueous solution of alkali salts of methionine with a reducing sulfur compound and neutralizing the decolorized solution with an acid (preferably sulfuric acid), or neutralizing the aqueous solution of alkali salts of methionine with an acid (preferably sulfuric acid) and decolorizing the solution with a reducing sulfur compound, and thereafter collecting methionine as colorless crystals from the resulting decolorized solution of methionine.

In the process of the invention, the decolorizing process may be carried out as a separate or independent operation, or it may be incorporated in the neutralizing process or the operaton of crystallizing methionine. However, good results may be obtained when it is conducted as an independent operation. In this case, the decolorizing process may be carried out by treating the aqueous solution of methionine or its alkali salts with a reducing sulfur compound, preferably at a temperature ranging from a room temperature to 200° C. for at least 10 minutes. In the case wherein the decolorizing process is incorporated in the neutralizing operation or the operation of crystallizing methionine, the decolorizing process can be carried out by subjecting the aqueous solution of methionine or its salts to these operations in the presence of a reducing sulfur compound under their ordinary operating conditions.

As reducing sulfur compounds used in the present invention, there may be exemplified sulfur dioxide, sulfites (e.g., sodium sulfite $Na_2SO_3$, ammonium sulfite $(NH_4)_2SO_3$, etc.,), bisulfites (e.g., sodium bisulfite $NaHSO_3$, ammonium bisulfite $(NH_4)HSO_3$, etc.,), disulfites (e.g., sodium disulfite $Na_2S_2O_5$, potassium disulfite $K_2S_2O_5$, etc.,), thiosulfates (e.g., sodium thiosulfate $Na_2S_2O_3$, potassium thiosulfate $K_2S_2O_3$, ammonium thiosulfate $(NH_4)_2S_2O_3$, etc.,), dithionites (e.g., sodium dithionite $Na_2S_2O_4$, etc.,), and a mixture thereof.

Among these sulfur compounds, particularly preferred are sulfites and sulfur dioxide. These sulfur compounds may be used in the form of aqueous solution or in the form of powders or gas. The amount of these sulfur compounds used in the decolorizing process is not particularly limited, but good results may be obtained when 0.005 to 10 parts by weight, preferably 0.01 to 1.0 parts by weight of the reducing sulfur compound is added to 100 parts by weight of the aqueous solution of methionine or its alkali salts to be decolorized.

In carrying out the process of the invention, the neutralization of the aqueous solution of alkali salts of methionine may advantageously be conducted when sulfuric acid is used because the reducing sulfur compounds are converted into sulfates during the decolorizing process.

According to the present invention, methionine devoid of a coloring matter can be obtained more economically as compared with the said known methods because, unlike the said known methods, the decolorizing process of the invention does not require any special arrangement for removal or disposal of the used materials, and only a small amount of the reducing sulfur compounds is used in the process. Further, the quality of the products is not decreased by the decolorizing process of the invention since the used reducing sulfur compounds are easily washed out from the products during the operations of collecting the products.

The following examples are given to illustrate the present invention more precisely, but it is not intended to limit the present invention thereto.

EXAMPLES 1 TO 8

235 g of 12.2% by weight aqueous solution of methionine sodium salt obtained by hydrolysis of MMH was neutralized with 22.4 g of 72% by weight sulfuric acid. To 250 g of 10% by weight aqueous solution of methionine obtained as above was added the reducing sulfur compound as given in the following Table I. The solution was refluxed at 100° C. for 30 minutes, and concentrated with an evaporator. The precipated crystals were collected and dried to give 19 g of colorless methionine.

The quantity of color of thus decolorized solution was measured by means of a spectrophotometer (made by HITACHI: 100-10 type) with 10 mm-cell at a wavelength 410, 440, and 470 nm using the saturated aqueous solution of methionine, which was obtained by cooling a small amount of the reflexed solution prepared as above to 20° C. and removing the precipitated crystals. As the blank, distilled water was used in the color quantity estimation. The results are given in the following Table I with reference to the percent transmittance.

TABLE I

| Example No. | Reducing sulfur compound added | Transmittance (%) | | |
|---|---|---|---|---|
| | | 410 nm | 440 nm | 470 nm |
| 1 | Sodium sulfite 0.5 g | 27.8 | 62.5 | 81.7 |
| 2 | Ammonium sulfite 0.5 g | 25.3 | 60.0 | 79.5 |
| 3 | Sodium disulfite 0.1 g | 29.0[3] | — | 79.8[3] |
| 4 | Ammonium disulfite 0.1 g | 20.5 | — | 65.5 |
| 5 | Sodium dithionite 0.2 g | 28.3[3] | — | 78.8[3] |
| 6 | Sodium thiosulfate 0.2 g | 17.3[3] | — | 62.8[3] |
| 7 | Sodium bisulfite 0.2 g | 20.5[3] | — | 72.5[3] |
| 8 | Sodium sulfite 0.2 g + Sodium thiosulfate 0.1 g | 23.0 | — | 78.3 |
| Comparison Example 1 | None | 6.3 | 24.3 | 44.3 |
| Comparison Example 2 | Activated carbons (0.2 g) was used instead of the reducing sulfur compound | 16.0 | 39.0 | 64.0 |

[1] In the Comparison Example 1, the experiment was carried out with the same procedures as in Example 1 without using the reducing sulfur compound.
[2] In the Comparison Example 2, the experiment was carried out with the same procedures in Example 1 using activated carbons (0.2 g) in place of the reducing sulfur compound.
[3] The measurement of the transmittance was carried out 6 days after the sample solution had been prepared.

EXAMPLES 9 to 13

To 150 g of the aqueous solution of methionine sodium salt containing 8.0% by weight of methionine sodium salt, which was prepared by hydrolysis of MMH was added 9.4 g of 72% by weight of sulfuric acid, and the reducing sulfur compound as given in the following Table II. The mixture was stirred at 80° C. for 60 minutes, and concentrated with an evaporator. The precipitated crystals were collected and dried to give 8 g of colorless methionine.

The color quantity measurement of the decolorized solution was conducted in the same manner as in Example 1. The results are given in the following Table II.

TABLE II

| Example No. | Reducing sulfur Compound added | Transmittance (%) | | |
|---|---|---|---|---|
| | | 410 nm | 440 nm | 470 nm |
| 9 | Sodium sulfite 0.5 g | 27.8 | 62.4 | 81.8 |
| 10 | Ammonium sulfite 0.5 g | 25.0 | 60.0 | 79.2 |
| 11 | Ammonium disulfite 0.1 g | 20.3 | — | 66.0 |
| 12 | Sulfur dioxide-gas 0.1N1 Sodium sulfite 0.5 g | 27.0 | — | 81.0 |
| 13 | + sulfur dioxide 0.05N1 | 27.9 | — | 82.0 |
| Comparison Example | None | 5.0 | 25.0 | 45.0 |

In the Comparison Example, the experiment was conducted in the same manner as in Example 9 without using the reducing sulfur compound.

What is claimed is:

1. A process for preparing colorless methionine from the aqueous solution of alkali salts of methionine prepared by hydrolysis of 5-($\beta$-methylmercaptoethyl)-hydantoin with an alkali, which comprises treating the said solution with a reducing sulfur compound before or during neutralizing the said solution with an acid, and thereafter collecting colorless methionine from the resulting decolorized solution of methionine, the reducing sulfur compound being sulfur dioxide, monosulfites, disulfites, bisulfites, thiosulfates, dithionites or a mixture thereof.

2. A process according to claim 1, wherein the sulfur compound is sulfur dioxide, monosulfites or a mixture thereof.

3. A process according to claim 1, wherein the amount of the reducing sulfur compound is 0.005 to 10% by weight of the solution to be treated.

4. A process according to claim 3, wherein the amount is 0.01 to 1.0% by weight of the solution to be treated.

5. A process according to claim 1, wherein the aqueous solution of alkali salts of methionine contains 2 to 20% by weight of alkali salts of methionine.

6. A process for preparing colorless methionine from the aqueous solution of alkali salts of methionine prepared by hydrolysis of 5-($\beta$-methylmercaptoethyl)-hydantoin with an alkali, which comprises treating an aqueous solution of methionine, which is obtained by neutralizing said solution with an acid, with a reducing sulfur compound, and thereafter collecting colorless methionine from the resulting decolorized solution of methionine, the reducing sulfur compound being sulfur dioxide, monosulfites, disulfites, bisulfites, thiosulfates, dithionites or a mixture thereof.

7. A process according to claim 6, wherein the reducing sulfur compound is sulfur dioxide, monosulfites or a mixture thereof.

8. A process according to claim 6, wherein the amount of the reducing sulfur compound is 0.005 to 10% by weight of the solution to be treated.

9. A process according to claim 8, wherein the amount is 0.01 to 1.0% by weight of the solution to be treated.

10. A process according to claim 6, wherein the aqueous solution of alkali salts of methionine contains 2 to 20% by weight of alkali salts of methionine.

* * * * *